(12) United States Patent
Mitchell et al.

(10) Patent No.: US 9,308,243 B2
(45) Date of Patent: Apr. 12, 2016

(54) CELLULAR ENHANCEMENTS IN BIOLOGICAL SYSTEMS THROUGH THE USE OF LI-POFULLERENE AND PEPTIDE GROUP COMBINATIONS

(71) Applicant: LivePet, LLC, Austin, TX (US)

(72) Inventors: Ian Mitchell, Bartlesville, OK (US); Ayyappan Subbiah, Bartlesville, OK (US); Daniel David Bensimon, Austin, TX (US)

(73) Assignee: LivePet, LLC, Austin, TX (US)

( * ) Notice: Subject to any disclaimer, the term of this patent is extended or adjusted under 35 U.S.C. 154(b) by 0 days.

(21) Appl. No.: 14/656,304

(22) Filed: Mar. 12, 2015

(65) Prior Publication Data
US 2015/0258181 A1    Sep. 17, 2015

Related U.S. Application Data

(60) Provisional application No. 61/953,706, filed on Mar. 14, 2014.

(51) Int. Cl.
*A61K 38/48*    (2006.01)
*A61K 38/07*    (2006.01)
*A61K 31/015*    (2006.01)

(52) U.S. Cl.
CPC ........... *A61K 38/4806* (2013.01); *A61K 31/015* (2013.01); *A61K 38/07* (2013.01)

(58) Field of Classification Search
None
See application file for complete search history.

(56) References Cited

U.S. PATENT DOCUMENTS

2009/0258841 A1    10/2009    Murphy et al.
2010/0040599 A1 *  2/2010    Yudoh ........................... 424/125

OTHER PUBLICATIONS

Kozina et al (Arch. Gerontol. Geriatr. S1:213-216 (2007).*
Drafi et al (Neuroendocrin. Let., 31(2):96-100 (2010).*
McPhee et al (Comp. Biochem. Phys., Part B, 146:346-356 (2007).*
Agostoni et al. "Scientific Opinion on the substantiation of health claims related to L-carnosine and increase in muscle power (ID 1824), increase in endurance capacity (ID 1824), "skin" (ID 1825) and maintenance of normal cardiac function (ID 1826) pursuant to Article 13(1) of Regulation (EC) No. 1924/20061", EFSA Journal 2011; 9(4):2038.
Andreichenko et al. "Effect of Fullerene C60 on ATPase Activity and Superprecipitation of Skeletal Muscle Actomyosin" ISSN 0201—8470. BioChem, 2013, m. 85, No. 2.
Andrievsky et al. "First clinical case of treatment of patient (volunteer) with rectal adenocarcinoma by hydrated C60 fullerenes: natural course of the disease or non-specific anticancer activity?"
Baati et al. "The prolongation of the lifespan of rats by repeated oral administration of [60] fullerene" Biomaterials xxx (2012) 1-11.
Bakry et al. "Medicinal applications of fullerenes" International Journal of Nanomedicine 2007:2(4) 639-649.
Boldyrev et al. "Carnosine, the Protective, Anti-aging Peptide" Bioscience Reports, vol. 19, No. 6, 1999.
Chen et al. "Applications of Functionalized Fullerenes in Tumor Theranostics" Theranostics 2012, 2(3):238-250.
Chistyakov et al. "Feasibility of the C60 Fullerene Antioxidant Properties: Study with Density Functional Theory Computer Modeling" Proceedings of the 2013 International Conference on Biology, Medical Physics, Medical Chemistry, Biochemistry and Biomedical Engineering.
Culbertson et al. "Effects of Beta-Alanine on Muscle Carnosine and Exercise Performance: A Review of the Current Literature" Nutrients 2010, 2, 75-98.
Grebowski et al. "Fullerenols as a New Therapeutic Approach in Nanomedicine" BioMed Research International vol. 2013, Article ID 751913, 9 pages.
Hipkiss et al. "Carnosine: can understanding its actions on energy metabolism and protein homeostasis inform its therapeutic potential?" Chemistry Central Journal 2013, 7:38.
Huczko et al. "Fullerenes: Experimental Evidence for a Null Risk of Skin Irritation and Allergy" Fullerene Science and Technology, 7(5), 935-939 (1999).
Johnston et al. "The Biological Mechanisms and Physicochemical Characteristics Responsible for Driving Fullerene Toxicity" Toxicological Sciences 114(2), 162-182 (2010).
Monti et al. "C60 Carboxyfullerene Exerts a Protective Activity against Oxidative Stress-Induced Apoptosis in Human Peripheral Blood Mononuclear Cells" Biochemical and Biophysical Research Communications 277, 711-717 (2000).
Murugesan et al. "Carbon inhibits vascular endothelial growth factor- and fibroblast growth factor-promoted angiogenesis" FEBS Letters 581 (2007) 1157-1160.
Prylutska et al. "Using water-soluble C60 fullerenes in anticancer therapy" Cancer Nano (2011) 2:105-110.

(Continued)

*Primary Examiner* — Blaine Lankford
*Assistant Examiner* — Thomas J Visone
(74) *Attorney, Agent, or Firm* — Meyertons, Hood, Kivlin, Kowert & Goetzel, P.C.; Eric B. Meyertons (57) ABSTRACT

In some embodiments, a chemical composition may include C60, serrapeptase, or a tetrapeptide. The tetrapeptide may include ALA,GLU,ASP,GLY. In some embodiments, the chemical composition may include a dipeptide. The dipeptide may include carnosine or camatine. In some embodiments, the chemical composition may include at least one lipid. One or more components of the chemical composition may be suspended in and/or dissolved in the at least one lipid. At least one lipid may include olive oil or mussel oil. In some embodiments, a method may include administering to a subject an effective amount of a pharmaceutically acceptable formulation comprising the chemical composition. The method may include inhibiting and/or ameliorating inflammation and/or a malady associated with inflammation. In some embodiments, the subject may include a human or a nonhuman mammal. Nonhuman mammals may include equines, canines, or felines.

16 Claims, 6 Drawing Sheets

(56) References Cited

OTHER PUBLICATIONS

Rajinikanth et al. "Investigations on the Potential of Serratiopeptidase—A Proteolytic Enzyme, on Acetic Acid Induced Ulcerative Colitis in Mice" Int J Pharm Pharm Sci, vol. 6, Issue 5, 525-531.
Sellman et al. "Serrapeptase an Amazing Gift from the Silk Worm" 2003.
Tsao et al. "In vitro action of carboxyfullerene" Journal of Antimicrobial Chemotherapy (2002) 49, 641-649.
Velasco et al. "Oxidative stability of virgin olive oil" Eur. J. Lipid Sci. Technol. 104 (2002) 661-676.
Yin et al. "The scavenging of reactive oxygen species and the potential for cell protection by functionalized fullerene materials" Biomaterials 30 (2009) 611-621.
Zhou "Liposome Formulation of Fullerene-Based Molecular Diagnostic and Therapeutic Agents" Pharmaceutics 2013, 5,525-541.
International Wellness Directory, http://www.mnwelldir.org/docs/terrain/chronic_inflammation.htm "Chronic Inflammation" 2007.

* cited by examiner

CELLULAR ENHANCEMENTS IN BIOLOGICAL SYSTEMS THROUGH THE USE OF LI-POFULLERENE AND PEPTIDE GROUP COMBINATIONS

PRIORITY CLAIM

This application claims priority to U.S. Provisional Patent Application No. 61/953,706 entitled "CELLULAR ENHANCEMENTS IN BIOLOGICAL SYSTEMS THROUGH THE USE OF LIPOFULLERENE AND PEPTIDE GROUP COMBINATIONS" filed on Mar. 14, 2014, which is incorporated by reference herein.

BACKGROUND OF THE INVENTION

1. Field of the Invention

The present disclosure generally relates to a pharmaceutically acceptable formulation inhibiting and/or ameliorating inflammation and/or a malady associated with inflammation. More particularly, the disclosure generally relates to a pharmaceutically acceptable formulation comprising a biologically compatible lipolized composition of C60, serrapeptase, and a tetrapeptide.

2. Description of the Relevant Art

The present disclosure relates to compositions based at least in part on fullerenes. Since the discovery of fullerenes, fullerenes have triggered interest in the scientific community based upon fullerenes interesting properties. Fullerene has been found to comprise a number of desirable structural, physical, and chemical properties adaptable for biological uses including antioxidants, anti-inflammatory, drug delivery, and photodynamic therapy.

Therefore a composition which better accentuates the antioxidant and/or anti-inflammatory properties of fullerenes would be highly desirable.

SUMMARY

In some embodiments, a chemical composition may include C60, serrapeptase, or a tetrapeptide. The tetrapeptide may include ALA,GLU,ASP,GLY. In some embodiments, the chemical composition may include a dipeptide. The dipeptide may include L-carnosine or L-carnitine. In some embodiments, the chemical composition may include at least one lipid. One or more components of the chemical composition may be suspended in and/or dissolved in the at least one lipid. At least one lipid may include olive oil or mussel oil. In some embodiments, a method may include administering to a subject an effective amount of a pharmaceutically acceptable formulation comprising the chemical composition. The method may include inhibiting and/or ameliorating inflammation and/or a malady associated with inflammation. In some embodiments, the subject may include a human or a nonhuman mammal. Nonhuman mammals may include equines, canines, or felines.

BRIEF DESCRIPTION OF THE DRAWINGS

Advantages of the present invention may become apparent to those skilled in the art with the benefit of the following detailed description of the preferred embodiments and upon reference to the accompanying drawings.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

\* \* \*

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning "having a feature that" performs the task or tasks during operation. As such, the component can be configured to perform the task even when the component is not currently on.

Various components may be described as performing a task or tasks, for convenience in the description. Such descriptions should be interpreted as including the phrase "configured to." Reciting a component that is configured to perform one or more tasks is expressly intended not to invoke 35 U.S.C. §112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The terms "administration," "administering," or the like, as used herein when used in the context of providing a pharmaceutical, cosmeceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The term "animal" as used herein generally refers to any member of the kingdom Animalia, comprising multicellular organisms that have a well-defined shape and usually limited growth, can move voluntarily, actively acquire food and digest it internally, and have sensory and nervous systems that allow them to respond rapidly to stimuli: some classification schemes also include protozoa and certain other single-celled eukaryotes that have motility and animal like nutritional modes. Generally the term animal as used herein does not refer to humans.

The term "anti-inflammatory" as used herein generally refers to a substance acting to reduce certain signs of inflammation (e.g., swelling, tenderness, fever, and pain).

The term "canine" as used herein generally refers to any of the biological family Canidae including carnivorous mammals including wolves, jackals, foxes, coyote, and the domestic dog.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The terms "effective concentration" or "effective amount" as used herein generally refers to a sufficient amount of the pharmaceutically active agent that is added to decrease, prevent or inhibit the growth of a virus and/or cancerous growth. The amount will vary for each compound and upon known factors related to the item or use to which the pharmaceutically active agent is applied.

The term "feline" as used herein generally refers to any of the biological family Felidae including lithe-bodied carnivorous mammals (as the lion, lynx, and cheetah, as well as the common house cat) having often strikingly patterned fur, comparatively short limbs with soft pads on the feet, usually sharp curved retractile claws, a broad and somewhat rounded head with short but powerful jaws equipped with teeth suited to grasping, tearing, and shearing through flesh, erect ears, and typically eyes with narrow or elliptical pupils and especially adapted for seeing in dim light.

The terms "in need of treatment" or "in need thereof" when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The term "malady" as used herein generally refers to any disorder or disease of the body or any undesirable or disordered condition including, but not limited to, illness, sickness, affliction, complaint, ailment, indisposition, virus, disease, fungus, infection, disease, etc.

The term "mammal" as used herein generally refers to any vertebrate of the class Mammalia, having the body more or less covered with hair, nourishing the young with milk from the mammary glands, and, with the exception of the egg-laying monotremes, giving birth to live young. Generally the term mammal as used herein does not refer to humans.

The terms "oligomeric" and "polymeric" as used herein are generally used interchangeably herein to generally refer to multimeric structures having more than one component monomer or subunit.

Terms such as "pharmaceutical composition," "pharmaceutical formulation," "pharmaceutical preparation," or the like, are used herein to generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

The term "pharmacologically inert," as used herein, generally refers to a compound, additive, binder, vehicle, and the like, that is substantially free of any pharmacologic or "drug-like" activity.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

The term "subject" as used herein generally refers to a mammal (e g, felines, canines), and in particular to a human.

The phrase "therapeutically effective amount" generally refers to an amount of a drug or pharmaceutical composition that will elicit at least one desired biological or physiological response of a cell, a tissue, a system, animal or human that is being sought by a researcher, veterinarian, physician or other caregiver.

Embodiments

Accordingly, there exists a need for an improved composition which better accentuates the antioxidant and/or anti-inflammatory properties of fullerenes.

In some embodiments, a method may include administering to a subject an effective amount of a pharmaceutically acceptable formulation comprising the chemical composition. The method may include inhibiting and/or ameliorating inflammation and/or a malady associated with inflammation. In some embodiments, the subject may include a human or a nonhuman mammal. Nonhuman mammals may include equines, canines, or felines.

In some embodiments, a chemical composition may be formed from naturally occurring compounds. The chemical composition may elicit an anti-inflammatory response. The chemical composition may elicit an anti-inflammatory response in subjects. The chemical composition may elicit an anti-inflammatory response in joints and muscles, improves immunity and/or helps remove scar tissue.

In some embodiments, a chemical composition may include one or more fullerenes. A fullerene is a molecule of carbon in the form of a hollow sphere, ellipsoid, tube, and many other shapes. Spherical fullerenes may be referred to as buckminsterfullerene or buckyballs or C60, and they resemble the balls used in soccer. Cylindrical fullerenes may be referred to as carbon nanotubes or buckytubes. Fullerenes are similar in structure to graphite, which is composed of stacked graphene sheets of linked hexagonal rings; but they may also contain pentagonal (or sometimes heptagonal) rings. Fullerenes are stable, but not unreactive. The $sp^2$-hybridized carbon atoms must be bent to form the closed sphere or tube, which produces angle strain. The characteristic reaction of fullerenes is electrophilic addition at 6,6-double bonds, which reduces angle strain by changing $sp^2$-hybridized carbons into $sp^a$-hybridized ones. The change in hybridized orbitals causes the bond angles to decrease from about 120° in the $sp^2$ orbitals to about 109.5° in the $sp^3$ orbitals. This decrease in bond angles allows for the bonds to bend less when closing the sphere or tube, and thus, the molecule becomes more stable.

Fullerenes have been used for several biomedical applications including the design of high-performance MRI contrast agents, X-Ray imaging contrast agents, photodynamic therapy and drug and gene delivery. Research on fullerene toxicity beginning in the early 1990s to present appears to conclude that very little evidence gathered since the discovery of fullerenes indicates that C60 is toxic. The toxicity of these carbon nanoparticles appears to be not only dose and time-dependent, but also depends on a number of other factors such as: type (e.g., C60, C70, functional groups used to water solubilize these nanoparticles (e.g., OH, COOH), and method of administration (e.g., intravenous, intraperitoneal)).

In some embodiments, a chemical composition may include buckminsterfullerene (Carbon 60 (C60)). C60 may function as an anti-oxidant and/or free radical scavenger assisting in maintaining good health. Fullerene C60 may function to inactivate hydroxyl radicals by attaching to the double bonds. The majority of reactive oxygen species (ROS) may be generated in mitochondrial respiratory chain and the presence of C60 inside the cells helps remove ROS.

Research involving the oral administration of C60 dissolved in olive oil ((lipofullerene) 0.8 mg/ml) at reiterated doses (1.7 mg/kg of body weight) to rats indicated no chronic toxicity. Rats treated with lipofullerene C60 demonstrated high resistance to carbon tetrachloride (CC14). Typically, administration of CC14 leads to adverse health effects ultimately leading to death. CC14 is known to trigger huge amounts of harmful reactive oxygen species in animals. Lipofullerene C60 was found to have high anti-oxidant activity in vivo protecting the $CCl_4$ exposed rats thus suggesting anti-oxidant capabilities of lipofullerene C60. The ability to scavenge free radicals by lipofullerene C60 by attaching to the double bonds is also known. It has been suggested that the mode of action is the attenuation of or decrease of age-associated oxidative stress.

In some embodiments, a chemical composition may include one or more lipids. Lipids are a group of naturally occurring molecules that include fats, waxes, sterols, fat-soluble vitamins (such as vitamins A, D, E, and K), monoglycerides, diglycerides, triglycerides, phospholipids, etc. The main biological functions of lipids include storing energy, signaling, and acting as structural components of cell membranes.

Lipids may be broadly defined as hydrophobic or amphiphilic small molecules. The amphiphilic nature of some lipids may allow them to form structures such as vesicles, multilamellar/unilamellar liposomes, or membranes in an aqueous environment. Biological lipids originate entirely or in part from two distinct types of biochemical subunits or "building-blocks" ketoacyl and isoprene groups. Using this approach, lipids may be divided into eight categories: fatty acids, glycerolipids, glycerophospholipids, sphingolipids, saccharolipids, polyketides, sterol lipids and prenol lipids.

Lipids may encompass molecules such as fatty acids and their derivatives (including tri-, di-, monoglycerides, and phospholipids), as well as other sterol-containing metabolites such as cholesterol. Although humans and other mammals use various biosynthetic pathways to both break down and synthesize lipids, some essential lipids cannot be made this way and must be obtained from the diet.

In some embodiments, one or more components of the chemical composition are suspended in and/or dissolved in at least one lipid. In some embodiments, at least one of the lipids may include olive oil. In some embodiments, at least one of the lipids may include mussel oil.

In some embodiments, a chemical composition may include one or more peptides. Peptides are naturally occurring biological molecules. Peptides are short chains of amino acid monomers linked by peptide (amide) bonds. The shortest peptides are dipeptides, consisting of 2 amino acids joined by a single peptide bond, followed by tripeptides, tetrapeptides, etc. In some embodiments, a chemical composition may include one or more polypeptides. A polypeptide is a long, continuous, and typically unbranched peptide chain. Hence, peptides fall under the broad chemical classes of biological oligomers and polymers, alongside nucleic acids, oligosaccharides and polysaccharides, etc.

In some embodiments, a chemical composition may include one or more tetrapeptides. Tetrapeptides have been shown to decrease the age-related changes in immune and neuroendocrine systems, and reduces the incidence of recurrent infections and chronic diseases. Tetrapeptides may include ALA,GLU,ASP,GLY (the sequence of amino acids in the peptide is L-Alanyl, L-Gluthamyl, L-Asparagyl, Glycine with a molecular formula of C14H22N409 (1)).

(1)

Geroprotective effects of the tetrapeptide have been demonstrated in various experiments. Studies have shown that the mode of action of the tetrapeptide involves suppression of oncogene expression and modification of telomerase activity. Tetrapeptides are known to help the proper functioning of endocrine, nervous and immune systems.

In some embodiments, a chemical composition may include one or more dipeptides. Dipeptides may include carnosine (e.g., L-Carnosine) or carnitine (e.g., L-Carnitine). L-Carnosine is a dipeptide of the amino acids beta-alanine and histidine. Research found that adding a tiny amount of carnosine to flies' food supply produced an immediate 20% increase in the average life span of male flies. The mode of action for this effect has been proven through scavenging reactive oxygen species (ROS).

Scavenging reactive oxygen species (ROS) by L-Carnosine may help build a healthy organism and a strong immune system. Oxidation of biopolymers by ROS plays a leading role in weakening of vital functions of aging organisms, and chemical compositions described herein helps alleviate that stress.

Advanced Glycation End (AGE) products are the subject of ongoing research. There are three therapeutic approaches: preventing the formation of AGEs, breaking crosslinks after they are formed, and preventing their negative effects. The free amino group derived from the alanine and the imidazole ring of histidine (Carnosine (2)) compete with amino groups of proteins in the presence of reactive dicarbonyl compounds (AGE products) responsible for aging. Amino groups of proteins react with dicarbonyl compounds forming AGE products and carnosine prevents forming AGE products.

(2)

In some embodiments, a chemical composition may include one or more proteolytic enzyme (proteases). A protease (also called peptidase or proteinase) is any enzyme that performs proteolysis, that is, begins protein catabolism by hydrolysis of the peptide bonds that link amino acids together in the polypeptide chain forming the protein. Proteases have evolved multiple times, and different classes of protease can perform the same reaction by completely different catalytic mechanisms. Proteases can be found in animals, plants, bacteria, archaea, and viruses.

In some embodiments, a chemical composition may include a protease such as serrapeptase. Serrapeptase (also known as *Serratia* E-15 protease, serralysin, serratiapeptase, *serratia* peptidase, serratio peptidase, or serrapeptidase) is a protease produced by *enterobacterium Serratia* sp. E-15. This microorganism was originally isolated in the late 1960s from silkworm *Bombyx Mori* L (intestine). Serratiopeptidase is present in the silkworm intestine and enables the emerging moth to dissolve its cocoon. Serratiopeptase is produced by purification from culture of *Serratia* E-15 bacteria. Serrapeptase supplements for human consumption are made from fermented enzymes extracted from the worms and marketed as an aid to normalize inflammatory response and improve overall tissue health. Studies indicate that serrapeptase showed better anti-inflammatory activity compared to other proteolytic enzymes.

Serrapeptase is a commonly used drug (Takeda Chemical Industries) in Japan and Europe. In the U.S., serrapeptase is classified as a dietary supplement. Serrapeptase is used for painful conditions including back pain, osteoarthritis, rheumatoid arthritis, osteoporosis, fibromyalgia, carpel tunnel syndrome, migraine headache, and tension headache.

In some embodiments, a chemical composition may include C60, serrapeptase, or a tetrapeptide. The tetrapeptide may include ALA,GLU,ASP,GLY. In some embodiments, the chemical composition may include a dipeptide. The dipeptide may include carnosine or carnitine. In some embodiments, the chemical composition may include at least one lipid. One or more components of the chemical composition may be suspended in and/or dissolved in the at least one lipid. At least one lipid may include olive oil or mussel oil. In some embodiments, a method may include administering to a subject an effective amount of a pharmaceutically acceptable formulation comprising the chemical composition. The method may include inhibiting and/or ameliorating inflammation and/or a malady associated with inflammation. In some embodiments, the subject may include a human or a nonhuman mammal. Nonhuman mammals may include equines, canines, or felines.

Dosage and Administration

In some embodiments, chemical compositions described herein may be administered at a dosage level up to conventional dosage levels, but will typically be less than about 50 mL per day. Suitable dosage levels for chemical compositions described herein may be about 0.01 mg to 10 mg per kg body weight of the patient per day, from about 0.1 mg to 1 mg per kg body weight of the patient per day, or from about 0.01 mg to 0.1 mg per kg body weight of the patient per day. The compound may be administered on a regimen of up to 6 times per day, between about 1 to 4 times per day, or once per day.

In the case where an oral composition is employed, a suitable dosage range is, e.g. from about 0.01 mg to about 10 mg per kg of body weight per day, preferably from about 0.1 mg to about 0.5 mg per kg.

It will be understood that the dosage of the therapeutic agents will vary with the nature and the severity of the condition to be treated, and with the particular therapeutic agents chosen. The dosage will also vary according to the age, weight, physical condition and response of the individual patient. The selection of the appropriate dosage for the individual patient is within the skills of a clinician.

In addition to administering chemical compositions described herein as described, the compounds may be administered as part of a pharmaceutical preparation containing suitable pharmaceutically acceptable carriers, preservatives, excipients and auxiliaries which facilitate processing of the chemical compositions described herein which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailability as described above, together with the excipient. While individual needs may vary, determination of the optimal ranges of effective amounts of each component is within the skill of the art.

General guidance in determining effective dose ranges for pharmacologically active compounds and compositions for use in the presently described embodiments may be found, for example, in the publications of the International Conference on Harmonisation and in REMINGTON'S PHARMACEUTICAL SCIENCES, 8$^{th}$ Edition Ed. Bertram G. Katzung, chapters 27 and 28, pp. 484-528 (Mack Publishing Company 1990) and yet further in BASIC & CLINICAL PHARMACOLOGY, chapters 5 and 66, (Lange Medical Books/ McGraw-Hill, New York, 2001).

Pharmaceutical Compositions

Chemical compositions described herein are typically administered orally but any suitable route of administration may be employed for providing a subject with an effective dosage of drugs of the chemical compositions described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally.

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the drugs used in the present invention are conveniently delivered in the form of an aerosol spray presentation from pressurized packs or nebulisers. The compounds may also be delivered as powders which may be formulated and the powder composition may be inhaled with the aid of an insufflation powder inhaler device.

Suitable topical formulations for use in the present embodiments may include transdermal devices, aerosols, creams, ointments, lotions, dusting powders, gels, and the like.

In practical use, drugs used can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives. Optionally, the resulting mixture may be ground and processed. The resulting mixture of granules may be used, after adding suitable auxiliaries, if desired or necessary, to obtain tablets, softgels, lozenges, capsules, or dragee cores.

The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

Liquid dosage forms for oral administration can contain coloring and flavoring to increase subject acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

In some embodiments, an oral composition may include a flavoring. A flavoring may include something an animal may find palatable. For example a flavoring may include malt extract, xylitol, splenda, sucralose or any sweetener. A flavoring may range from 0.01% to 0.10%, 0.10% to 1.0%, or 1.0% to 10.0% of a composition.

In some embodiments, a composition may include a colorant. A colorant may include D&C Blue #1 or any FDA approved color. A colorant may range from 0.001% to 0.010%, 0.010% to 0.10%, or 0.10% to 1.0% of a composition.

Additional oral compositions which may be used to deliver chemical compositions described herein, as well as additional uses, are described in U.S. Pat. No. 4,666,896 to Warner, Jr. et al., U.S. Pat. No. 5,393,516 to Rheinberger et al., and U.S. Pat. No. 5,948,390 to Nelson et al., as well as U.S. Patent Publication No. 2005/0158252 to Romanowski et al., which are incorporated by reference as if fully set forth herein.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas. Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include, but are not limited to, suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Liposomal formulations, in which mixtures of the chemical compositions described herein with, for example, egg yolk phosphotidylcholine (E-PC), may be made for injection. Optionally, the suspension may contain stabilizers, for example, antioxidants such as BHT, and/or preservatives, such as benzyl alcohol.

In some embodiments, an oral composition may include a fragrance.

In some embodiments, a composition may include additional additives which may function in combination or separately from the chemical compositions described herein in solution. Additives may function to improve a subject's health. Additives may include vitamins including, but not limited to, vitamins D and E.

In some embodiments, different compositions may be formulated for different types of users. For professionals users (e.g., doctors, vetenaries), compositions may include a greater percentage of chemical compositions described herein than compositions formulated for over the counter sale to nonprofessionals. Professional compositions may not include flavorings or colorants.

While previous discussions herein have concentrated on the use of chemical compositions described herein for treating maladies associated with oral cavities of humans and animals. Chemical compositions described herein may be used for the inhibition and/or amelioration of various maladies associated with humans and/or more particularly animals. Malidies inhibited and/or ameliorated may include diseases, parasites, viruses, infections, wounds, etc.

While previous discussions herein have concentrated on the use of chemical compositions described herein for treating maladies animals such as common household pets including canines and felines, these examples should not be seen as limiting. Compositions described herein may be used to treat other animals (e.g., mammals) including, but not limited to, avian (birds), reptiles, horses, swine, sheep, goats, deer, tigers, protein producing animals (e.g., cattle), and/or lions. Compositions described herein may be used to treat humans

EXAMPLES

Having now described the invention, the same will be more readily understood through reference to the following example(s), which are provided by way of illustration, and are not intended to be limiting of the present invention.

General Experimental: Companion 60 consists of LPM-Base and LPM252. LPM-Base is lipofullerene (~0.8 g of C60 in oil) and LPM252 is the combination of ALA,GLU,ASP, GLY tetra peptide, L-camosine dipeptide and serrapeptase a proteolytic enzyme.

Preparation of LPM-Base: About 1000 ml of virgin olive oil obtained from "Time Olive Oil" company was stirred with 0.8 grams of 99.99% pure Carbon-60 which was obtained from SES research. The stirring process was carried out at 38 C and for a period of 14 days in the absence of light. After the completion of stirring, the solution was filtered using quantitative 103 slow filter paper. The filtrate is treated as the base (LPM-Base).

Preparation of Companion 60: 1000 ml of LPM-Base is stirred with LPM252 for about an hour. LPM252 consists of (1). ALA,GLU,ASP,GLY, (2). Carnosine and (3).

Serrapeptidase in the following proportion: About 100 mg of ALA,GLU,ASP,GLY is added to 1000 ml of LPM-Base and stirred for minimum of 30 minutes. Then 10 grams of carnosine is added to the above solution and stirred for another 30 minutes followed by adding 20 capsules of 250, 000 SPU $Serratia$ and continuing the stirring for another 30 minutes. The final product is cloudy and stored at room temperature and away from light. The final product is shaken well before any use.

ALA,GLU,ASP,GLY is a tetra peptide made from four amino acids (L-Alanyl, L-Gluthamyl, L-Asparagyl, Glycine). It has a molecular weight of 390.35 and a molecular formula is C14H22N4O9. It has also been shown to be secreted by the pineal gland in animal test subjects. ALA, GLU,ASP,GLY was obtained from GenScript labs, Piscataway, N.J.

L-Carnosine is a dipeptide found primarily in red meat. Highly concentrated in brain and muscle tissue (including the heart), and delays aging in laboratory animals and human tissues. It was obtained from Premier Research Labs, Austin, Tex.

Serratiopeptidase or serrapeptase is a proteolytic (protein digesting) enzyme originally discovered in the intestine of silkworms. It is commercially called as $Serratia$ (250,000 SPU) and obtained from Arthur Andrew Medical, Scottsdale, Ariz.

Safety and Efficacy Tests
Materials and Methods
Study Protocol, Amendments, and Deviations:
There were three Protocol Deviations prepared following study completion detailing Physical Examinations that were scheduled for Study Day 35 but were conducted on Study Day 32, missed data on Pain Inventory Questionnaires and one missed mortality check. These deviations had no impact on the outcome of the study.

Test Articles: The test compound was initially received on 2 Oct. 14 and was assigned LRI ID number T-14-0028. Four additional flasks of test compound were received on 17 Oct. 14. The control article was received on 6 Oct. 14 and was assigned LRI ID number T-14-0029. Cosequin® was received on 6 Oct. 14 and was assigned LRI ID number T-14-0030. Dasuquin® for Dogs under 60 lbs was received on 6 Oct. 14 and was assigned LRI ID number T-14-0031. Two additional bottles of Dasuquin for Dogs under 60 lbs were received on 20 Oct. 14. Dasuquin® for Dogs over 60 lbs was received on 6 Oct. 14 and was assigned LRI ID number T-14-0031. All test and control compounds were stored at room temperature in a secure area at the testing facility. All remaining test article was returned to the Sponsor on 25 Nov. 14.

Animals: A copy of the animal procurement and disposition records are presented in Appendix 3. Fifteen hounds (female) and 1 beagle (male) were received from Covance Research Products, Inc. on 8 Sep. 14, 10 beagles (female) were received from Ridglan Farms, Inc. on 16 Sep. 14 and 9 beagles (8 female and 1 male) were received from the LRI colony on 19 Sep. 14.

These 35 animals were randomly assigned to one of seven treatment groups on Study Day −3. Following study completion, all animals were returned to LRI colony.

Housing and Environmental Conditions: All animals were individually housed and were separated by group. Temperatures were maintained by a central forced air gas furnace and air conditioning system. Study room temperature and relative humidity ranged from 53.0° F. to 73.8° F. and too low to register on the hygrometer to 74%, respectively in Iso 2 Room 1, from 53.2° F. to 84.0° F. and too low to register on the hygrometer to 75%, respectively in Iso 2 Room 2, from 64.2° F. to 75.6° F. and too low to register on the hygrometer to 63%, respectively in Iso 8 Room 1 and from 65.0° F. to 77.6° F. and 20% to 63%, respectively in Iso 8 Room 2. Overhead fluorescent lights on an automated 12-hour light/dark cycle were maintained throughout the study with brief interruptions for study activities. Sanitization was performed every two weeks for pens and weekly for food and water bowls.

Feed and Water Management: Diet was available to all animals ad libitum.

Beginning on Study Day −3, food consumption was measured.

Fresh well water was available to all animals ad libitum throughout the study. Neither the Sponsor nor the Study Director was aware of any potential contaminants likely to be present in the drinking water that interferes with the results of this study.

Acclimation of Test Animals: The dogs acclimated to the study environment for ten days prior to the initial treatment. Blood samples were collected on Study Day −7, Physical Examinations and Pain Inventories were performed on Study Day −3 and body weights were collection on Study Day −1. Daily Pain Assessments were performed once daily during the exercise period and Mortality Checks were conducted twice daily throughout acclimation.

Inclusion Criteria: All animals used were in good overall health, had no behavioral problems and were between 4 and 8 years of age at study initiation. Examination by the Attending Veterinarian revealed health issues appropriate for the age of the animals. These findings included interdigital cysts between the toes, pressure sores, lick granulomas, soft mammary masses, eye discoloration and dental tartar.

Veterinary Care: The Staff Veterinarian was authorized to treat animals for non-study related health problems and to treat or euthanize, if appropriate. For the treatment of interdigital cysts in several animals, technicians soaked the affected feet in an Epsom Salt bath.

Randomization: Details of the randomization procedure and animal assignment to a treatment group are presented in Appendix 5. The animals were separated by breed (mongrel/beagle), then ranked by ascending Quality of Life (QoL) Scores obtained using a questionnaire based on the Canine Brief Pain Inventory (CBPI). Treatment Groups were then alternately assigned (i.e. 1, 2, 3, 4, 5, 6, 7, 1, 2, etc.).

Masking of Study: Personnel that performed observations were masked to treatment throughout the study.

Dosing Regimen and Administration: Groups 1, 2, 3, 4, and 5 received the vehicle/test compound for three consecutive days beginning on Study Day 0, then every other day for the duration of the study. Groups 6 and 7 received the over the counter anti-inflammatory medications daily beginning on Study Day 0. The table below outlines the dosing regimen and administration by group.

| Group | No. of Dogs | Drug | Dose | Route | Treatment Day |
|---|---|---|---|---|---|
| 1 | 5 | Olive Oil | 0.5 mg/kg | Oral | Three consecutive days beginning on Study Day 0, then every other day for the duration of the study |
| 2 | 5 | Test Compound (½X) | 0.25 mg/kg | Oral | Three consecutive days beginning on Study Day 0, then every other day for the duration of the study |
| 3 | 5 | Test Compound (1X) | 0.5 mg/kg | Oral | Three consecutive days beginning on Study Day 0, then every other day for the duration of the study |
| 4 | 5 | Test Compound (3X) | 1.5 mg/kg | Oral | Three consecutive days beginning on Study Day 0, then every other day for the duration of the study |
| 5 | 5 | Test Compound (5X) | 2.5 mg/kg | Oral | Three consecutive days beginning on Study Day 0, then every other day for the duration of the study |
| 6 | 5 | Cosequin ® | Per label instruction | Oral | Daily |
| 7 | 5 | Dasuquin ® | Per label instruction | Oral | Daily |

Administration of the test compound was well tolerated with no indication that it was not palatable.

Sample Collection and Analysis

Cytokine Analysis: Blood samples were collected in serum separator tubes from all animals on Study Days −7, 0, 7, 14, 21, 28 and 35. The serum was separated and stored at ≈−80° C. Following study completion, serum samples from Study Days 0, 7, 14, 21, 28 and 35 were sent to Eurofins Pharma Bioanalytics Services US, Inc. for cytokine analysis.

Pharmacokinetic Data: Blood samples to determine pharmacokinetic parameters for the test compound were collected from all Group 3 animals prior to treatment and at 0, 0.5, 1, 2, 4, 8 hours posttreatment on Study Day 0 and 24 hours posttreatment on Study Day 1. The samples were processed, stored at ≈−80° C. and retained to be analyzed at a later time.

Clinical Pathology: In order to obtain safety data, at baseline (prior to the first does) and at study completion, blood samples were collected from the animals in Groups 1, 3, 4 and 5. The following analyses were conducted:

| | |
|---|---|
| ☐ CBC | ☐ Potassium |
| ☐ Blood urea nitrogen | ☐ Sodium/potassium ratio |
| ☐ Creatinine | ☐ Anion gap |
| ☐ Glucose | ☐ Cholesterol |
| ☐ Calcium | ☐ Triclyceride levels |
| ☐ Sodium | ☐ Phosphate |
| ☐ Chloride | ☐ Bicarbonate |

Urinalysis: Urine samples were collected via catheterization or cystocentesis at baseline and at study completion. The following analyses were conducted:

| | | |
|---|---|---|
| ☐ Color | ☐ Appearance | ☐ Specific gravity |
| ☐ pH | ☐ protein | ☐ glucose |
| ☐ ketone | ☐ bilirubin | ☐ blood |
| ☐ white blood cells | ☐ red blood cells | ☐ casts |
| ☐ crystals | ☐ bacteria | ☐ Squamous epithelia |

Results

Physical Examinations: All animals were noted to be in good general health during physical examination and any findings noted were considered appropriate for the age of the animals.

Daily Pain Assessments: All observations were considered incidental and not related to test or control article administration.

Adverse Events: There were no Adverse Events reported during the course of the study. Observations of interdigital cysts, lick granulomas and other various skin irritations were noted in all groups prior to as well as following administration of the control article, test compound and over the counter anti-inflammatory products.

Quality of Life Scoring (QoL): The biggest decrease in pain and interference with function score as well as increase in range of motion was noted in Group 3. The lowest change in the same parameters was noted in Group 1. This indicates that administration of the test compound at the therapeutic level led to a larger increase in the quality of life than the over the counter anti-inflammatory products administered to Groups 6 and 7.

Body Weights: No notable increase or decrease in body weight changes were observed between groups over the course of the study.

Food Consumption: No notable increase or decrease in food consumption data were observed between groups over the course of the study.

Oxygen Saturation: No notable changes in blood oxygen saturation levels were observed between groups over the course of the study.

Figure 1:
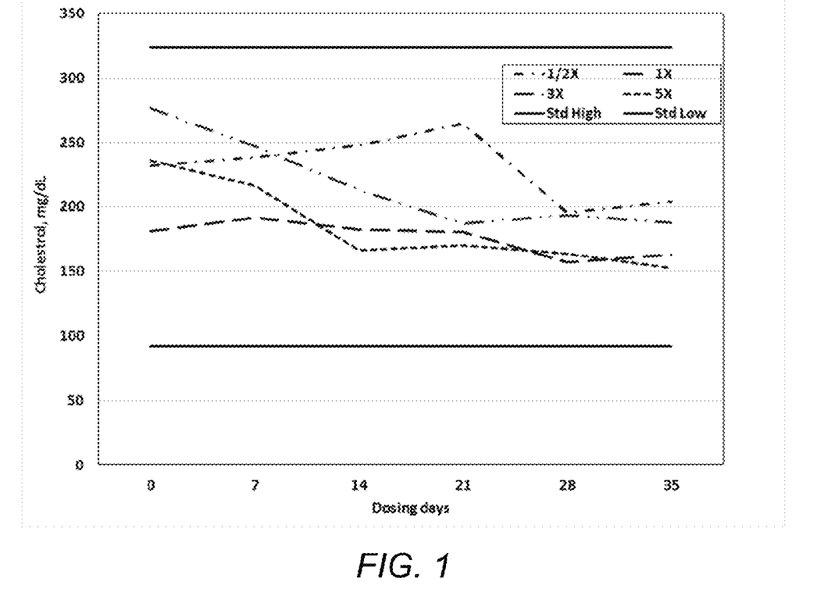
FIG. 1 depicts a graphical representation of a result of a blood serum analysis of cholesterol after dosing a first group of canines with a chemical composition.
Figure 2:
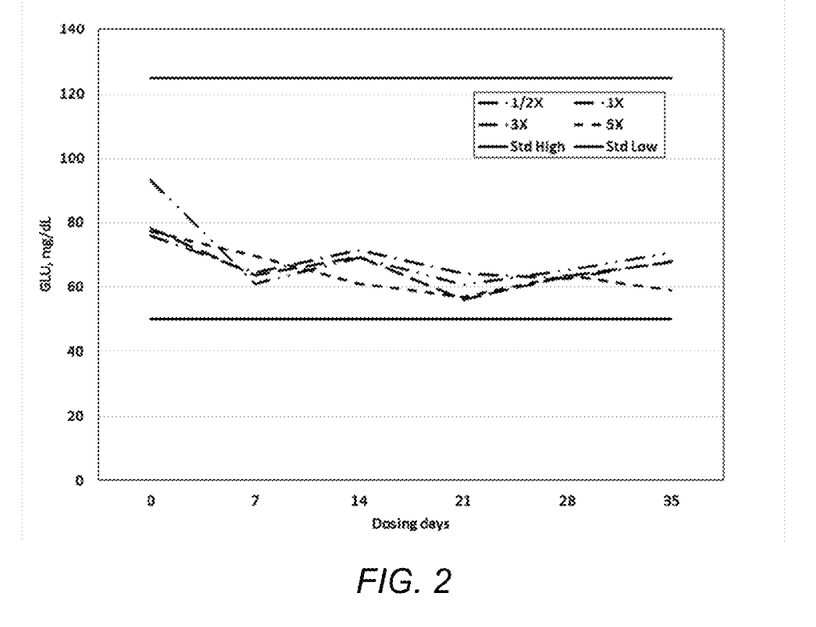
FIG. 2 depicts a graphical representation of a result of a blood serum analysis of glucose after dosing a first group of canines with a chemical composition.
Figure 3:
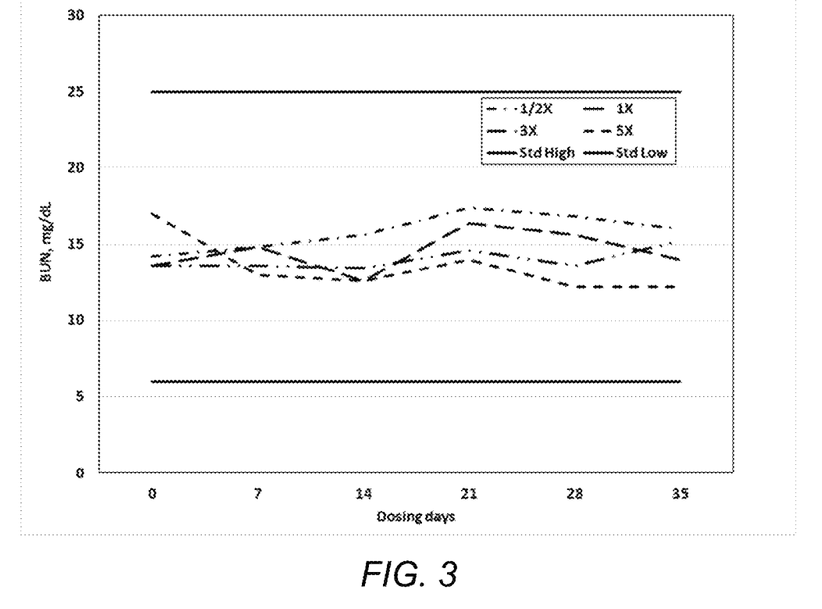
FIG. 3 depicts a graphical representation of a result of a blood serum analysis of blood urea nitrogen after dosing a first group of canines with a chemical composition.
Figure 4:
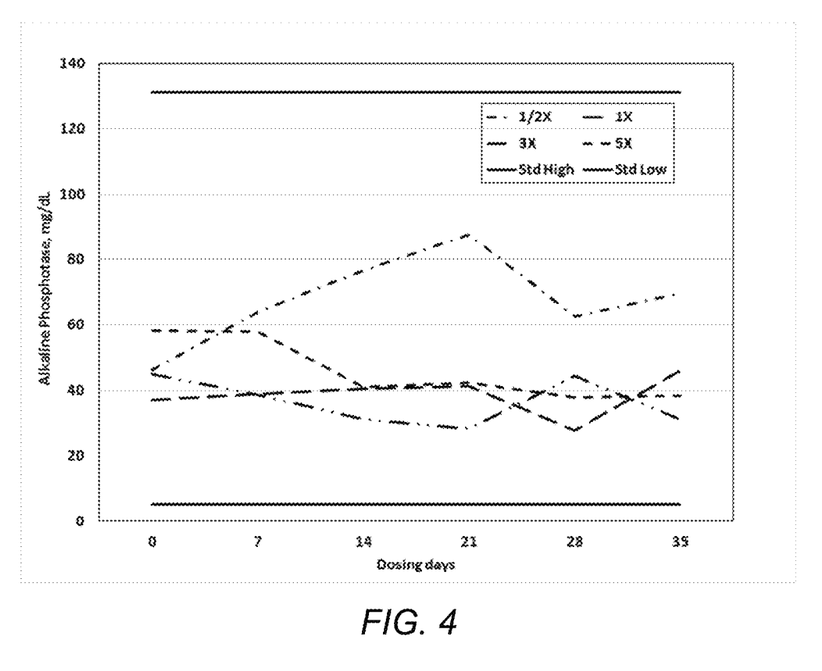
FIG. 4 depicts a graphical representation of a result of a blood serum analysis of alkaline phosphotase after dosing a first group of canines with a chemical composition.
Figure 5:
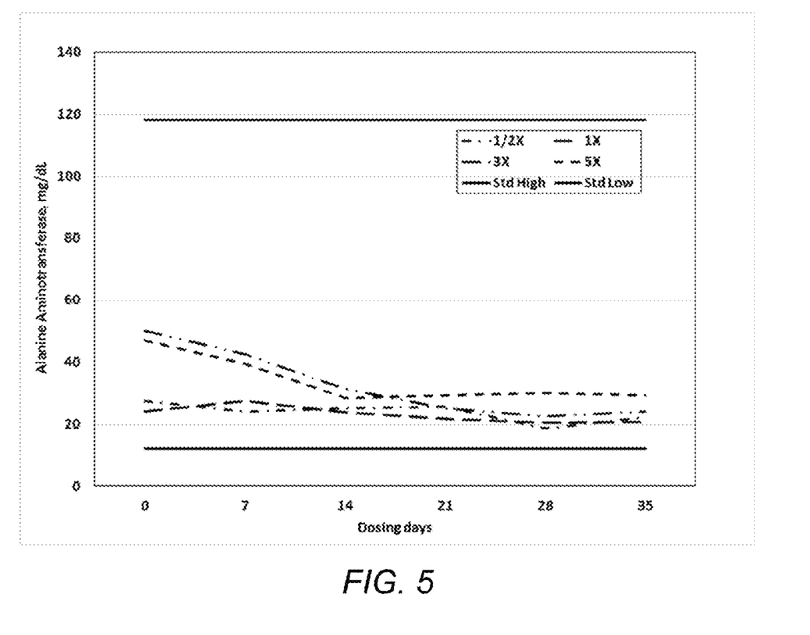
FIG. 5 depicts a graphical representation of a result of a blood serum analysis of alanine aminotransferase after dosing a first group of canines with a chemical composition.
Figure 6:
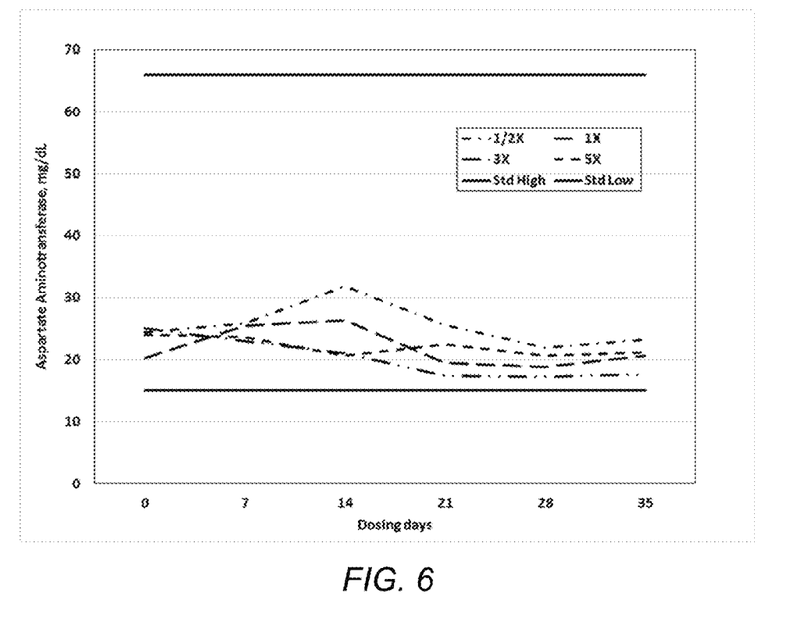
FIG. 6 depicts a graphical representation of a result of a blood serum analysis of aspartate aminotransferase after dosing a first group of canines with a chemical composition.
Figure 7:
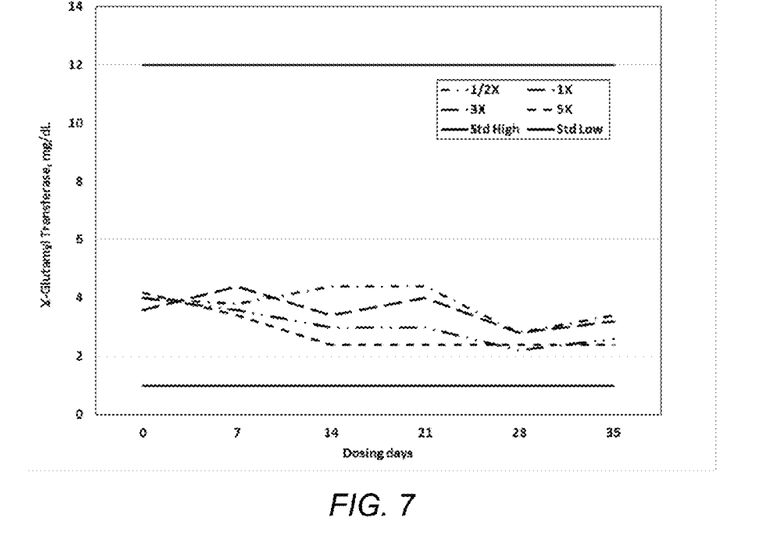
FIG. 7 depicts a graphical representation of a result of a blood serum analysis of gamma glutamyl transferase after dosing a first group of canines with a chemical composition.
Figure 8:
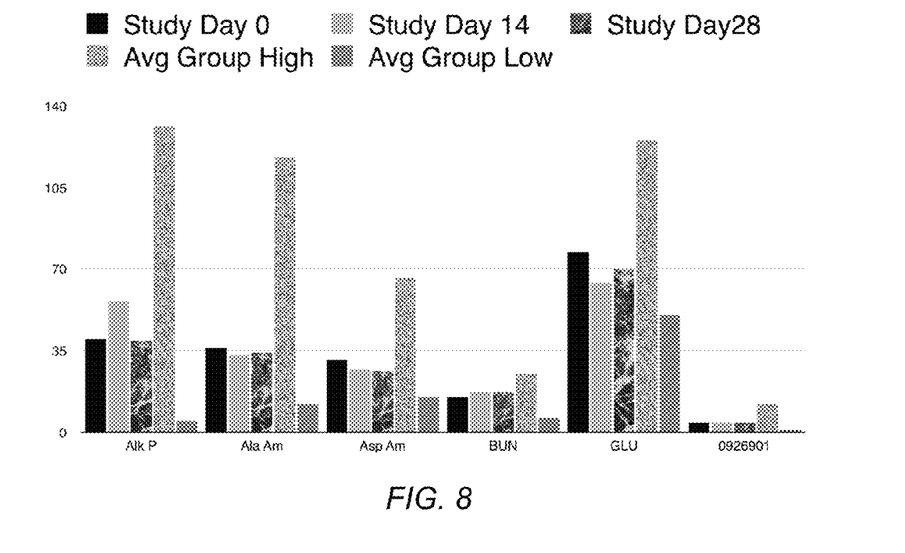
FIG. 8 depicts a graphical representation of a result of a blood serum analysis of several liver enzymes after dosing a second group of canines with a chemical composition.

Blood serum analysis for the liver enzymes (Trial 1): Trial 1 blood samples from all of the dogs were collected from 0, 7, 14, 21, 28 and 35th day of dosing. Various liver enzymes were tracked during the trial period which ranged from 0 to 35 days. Liver enzymes were analyzed from the blood serum samples using a liver-panel. The liver panel analytes were Cholestrol, GLU (Glucose), BUN (Blood Urea Nitrogen), alkaline phosphotase, Alanine Aminotransferase, Aspartate Aminotransferase, gamma Glutamyl Transferase. The analyte values are averaged for each group containing 5 dogs and plotted against the dosing days, starting from 0 to 35 days, as depicted in FIGS. 1-7. The normal standard low and high values are indicated in the graph as solid straight lines for reference. The analysis of the graphs indicate that the values remain within the normal range even after the 35th day of treatment for all of the treated groups (½×, 1×, 3× and 5×). These results indicate that treating with chemical compositions described herein is safe for the dogs even at high level of dosing. FIG. 8 depicts a graphical representation of a result of a blood serum analysis of several liver enzymes after dosing a second group of canines with a chemical composition.

Clinical Pathology Analysis: Cytokine Analysis: The table below indicates which cytokines were analyzed.

| Pro-Inflammatory | Anti-Inflammatory |
| --- | --- |
| GM-CSF | IL-7 |
| IFNa | IP-10 |
| IL-6 | IL-10 |
| IL-8 | |
| IL-15 | |
| MCP-1 | |
| TNFa | |
| IL-2 | |
| KC | |

A decrease in pro-inflammatory cytokines was noted for most animals treated with the test compound following all weeks of dosing. These numbers, however, increased again following the second week of dosing and continued this pattern throughout the study. This may be correlated to the when blood was collected in relation to the last dose administration. When blood samples were collected approximately 24 hours following test compound administration (Days 7, 21 and 35), a decrease in pro-inflammatory cytokines was noted indicating a decrease in inflammation. When blood samples were collected approximately 2 hours following test compound administration (Days 14 and 28), an increase in these cytokines was noted. The previous test compound administration occurred approximately 51 hours prior to this sampling. Indicating that metabolization of the test compound does not occur within 2 hours of administration and the decrease in pro-inflammatory cytokines does not last 51 hours.

Figure 9:
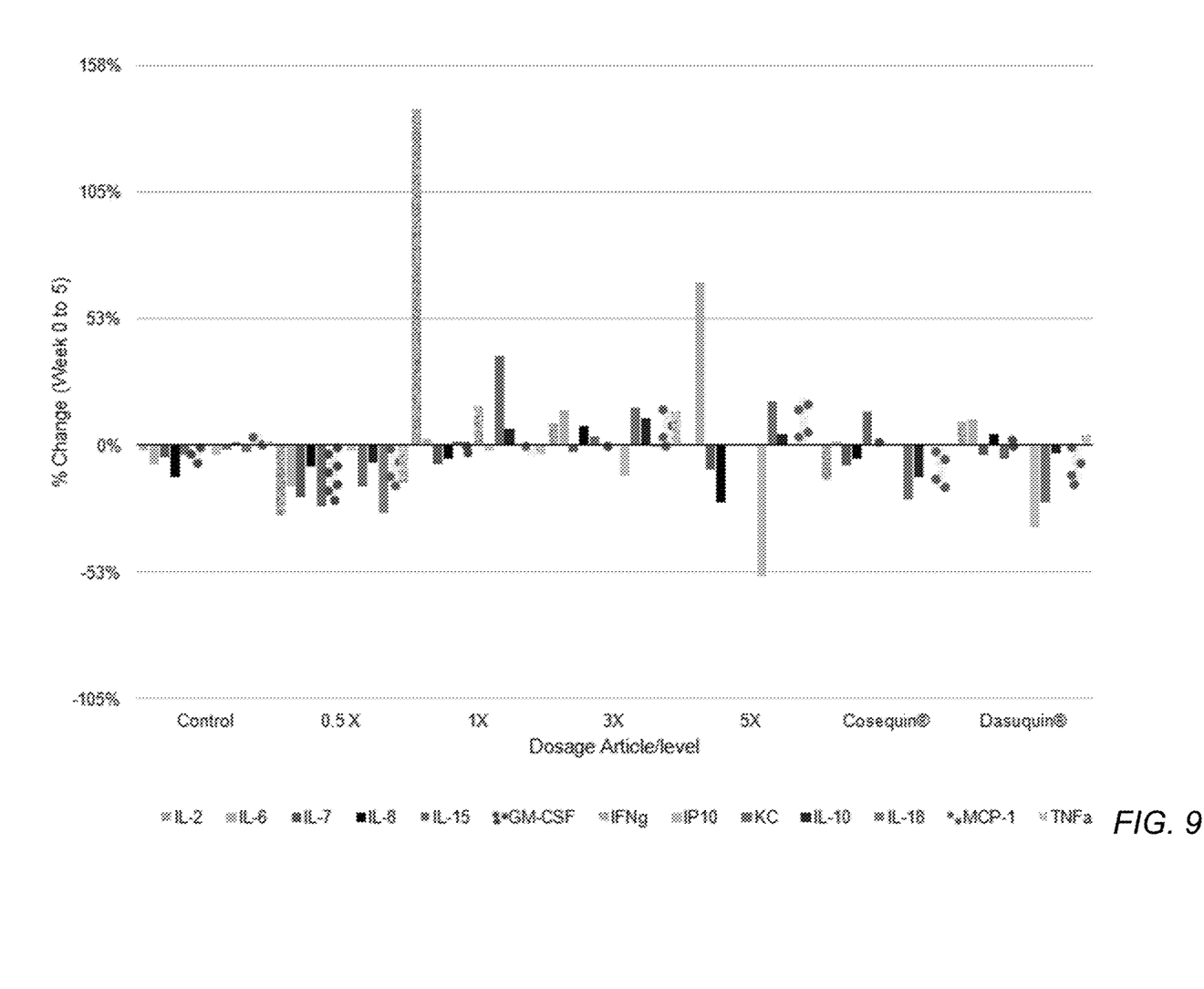
FIG. 9 depicts a graphical representation of a result of a cytokine analysis.
Figure 10:
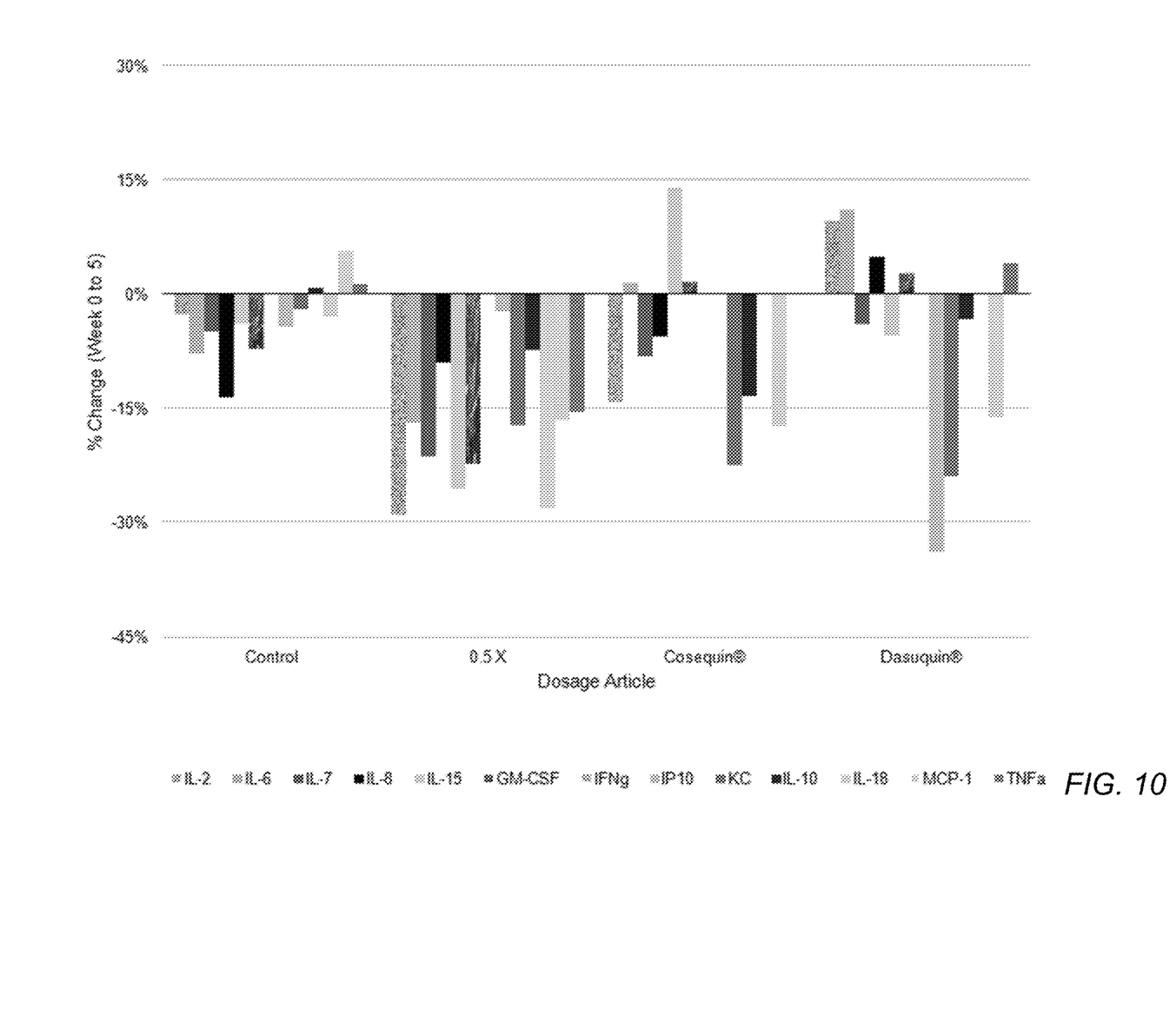
FIG. 10 depicts the control group, the proper dosage for companion 60 group, and the two competitors that were involved in clinical trial 1.

During the clinical trial (Trial 1), blood samples from all the dogs were collected after 0, 7, 14, 21, 28 and 35th day of dosing. Selected canine anti-inflammatory blood markers such as IL-2, IL-6, IL-7, IL-8, IL-15, IL-18, KC, MCP-1 and INFa were analyzed on the collected blood serum samples. Only selected dogs expressed the blood markers (above the detection limit of the instrument) and the graphs are provided below. The graph depicted in FIG. 9 indicates that the corresponding blood markers go down in value after the LivePet serum dosing for 35 days. FIG. 10 depicts the control group, the proper dosage for Companion 60 group, and the two competitors that were involved in clinical trial 1. As depicted in FIG. 10 a decrease in all of the cytokine levels for the group administered Companion 60 relative to the control group and relative to most of the cytokines relative to Cosequin® and Dasuquin® (both commercially available products which are advertised as treating joint health (i.e., anti-inflammatory compositions).

When comparing the Group average from Study Day 0 to those from Study Day 35, Group 2 showed a decrease in all cytokine levels with the exception of IFNg which did not change. These decreases ranged from a 2.35% decrease in IP-10 to a 29.05% decrease in IL-2 with an average decrease of 16.28%. Groups 6 and 7 showed a decrease in 6 out of 13 cytokines analyzed with no change noted in IFNg in either group and no change in IP-10 noted in Group 6.

Hematology Analysis: No notable changes in hematology parameters were observed between groups over the course of the study.

Serum Chemistry Analysis: No notable changes in serum chemistry parameters were observed between groups over the course of the study.

Urinalysis: No notable changes in urinalysis parameters were observed between groups over the course of the study.

Anecdotal evidence from humans using Companion 60: One of the company partners had rheumatic fever as a child and as such has rheumatoid arthritis. He had not been able to fully close his right hand for over 4 years and within 5 months of taking Companion 60 was again able to do so.

One woman in her late sixties had inpatient surgery for an invasive fistula and afterwards took Companion 60 to assist with her recovery. 10 days post-surgery, she was able to kayak farther than she had ever been able to go previously.

A doctor in his late 50's had arthritis affecting his ability to place pressure on his left hand and after taking Companion 60 for 3 weeks was again able to do so.

A company partner partially dislocated his shoulder and damaged a ligament. Companion 60 helped alleviate the swelling and assist in recovery of mobility.

One woman in her late forties took Companion 60 after experiencing a major loss of joint mobility due to inflammation. She was not able to twist from side to side or bend over. After taking Companion 60, she regained full mobility within a day hours. She said it felt as if her spine had been lubricated and was on a swivel.

Discussion & Conclusions

Dosing with the test compound was well tolerated and palatable at all dose levels (0.5×, 1×, 3× and 5×) when administered for three consecutive days and then every other day for a total of 19 dose administrations. No adverse effects related to administration of the test compound were noted in any groups. No notable changes in body weights, food consumption, blood oxygen saturation, clinical pathology or urinalysis were noted. The largest increase in Quality of life was noted in Group 3, the group receiving the test compound at the therapeutic dose level. The smallest increase in quality of life was noted in Group 1, the animals receiving the control article. A greater increase in activity level and mobility was also noted in Group 3 when compared to Groups 6 and 7, the groups receiving the over the counter anti-inflammatory products. The decrease in pro-inflammatory cytokines following one week of dosing in animals receiving the test compound indicated a decrease in inflammation. This decrease in inflammation was also indicated by the decrease in the group averages of 12 out of 13 cytokines in Group 2 which received the test compound at 0.5× the therapeutic dose. The 0.5× Group performed the best out of all the groups tested.

In conclusion, administration of the test compound at 0.5×, 1×, 3× and 5× the therapeutic dose did not indicate any toxicity, was efficacious in improving the quality of life in dogs over 3 years of age when compared to the over the counter anti-inflammatory products administered and showed a decrease in inflammation with optimal decrease in pro-inflammatory cytokines occurring in animals treated with the test compound at half the therapeutic dose when blood samples were collected approximately 24 hours following test compound administration.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A chemical composition, comprising:
   C60;
   serrapeptase;
   a dipeptide, wherein the dipeptide comprises carnosine; and
   a tetrapeptide, wherein the tetrapeptide comprises ALA-GLU-ASP-GLY.

2. The chemical composition of claim 1, further comprising at least one lipid.

3. The chemical composition of claim 1, further comprising at least one lipid, wherein one or more components of the chemical composition are suspended in and/or dissolved in the at least one lipid.

4. The chemical composition of claim 1, further comprising at least one lipid, wherein the at least one lipid comprises olive oil.

5. The chemical composition of claim 1, further comprising at least one lipid, wherein the at least one lipid comprises mussel oil.

6. A chemical composition, comprising:
   C60;
   at least one lipid, wherein one or more components of the chemical composition are suspended in and/or dissolved in the at least one lipid;
   serrapeptase;
   carnosine; and
   a tetrapeptide, wherein the tetrapeptide comprises ALA-GLU-ASP-GLY.

7. A method of inhibiting and/or ameliorating inflammation and/or a malady associated with inflammation, comprising:
   administering to a subject an effective amount of a pharmaceutically acceptable formulation comprising a chemical composition comprising:
   C60;
   serrapeptase;
   a dipeptide, wherein the dipeptide comprises carnosine; and
   a tetrapeptide, wherein the tetrapeptide comprises ALA-GLU-ASP-GLY;
   inhibiting and/or ameliorating inflammation and/or a malady associated with inflammation.

8. The method of claim 7, wherein the subject comprises a nonhuman animal.

9. The method of claim 7, wherein the subject comprises a nonhuman mammal.

10. The method of claim 7, wherein the subject comprises an equine, canine, or feline.

11. The method of claim 7, wherein the subject comprises a human.

12. The method of claim 7, further comprising at least one lipid.

13. The method of claim 7, further comprising at least one lipid, wherein one or more components of the chemical composition are suspended in and/or dissolved in the at least one lipid.

14. The method of claim 7, further comprising at least one lipid, wherein the at least one lipid comprises olive oil.

15. The method of claim 7, further comprising at least one lipid, wherein the at least one lipid comprises mussel oil.

16. The method of claim 7, wherein inhibiting and/or ameliorating inflammation and/or a malady associated with inflammation comprises inhibiting induction of interleukin 6 (IL-6) expressions.

* * * * *